(12) United States Patent
Victor

(10) Patent No.: US 9,125,670 B1
(45) Date of Patent: Sep. 8, 2015

(54) TILTED BLADE HEMISPHERICAL BONE CUTTER

(71) Applicant: Greatbatch Ltd., Clarence, NY (US)

(72) Inventor: Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/188,515

(22) Filed: Feb. 24, 2014

Related U.S. Application Data

(60) Provisional application No. 61/768,159, filed on Feb. 22, 2013.

(51) Int. Cl.
*A61B 17/16* (2006.01)

(52) U.S. Cl.
CPC ......... *A61B 17/1666* (2013.01); *A61B 17/1662* (2013.01); *A61B 17/1664* (2013.01)

(58) Field of Classification Search
CPC ............... A61B 17/16; A61B 17/1662; A61B 17/1664; A61B 17/1666; B23C 3/023; B23C 5/12; B23C 5/14
See application file for complete search history.

(56) References Cited

U.S. PATENT DOCUMENTS

| | | | |
|---|---|---|---|
| 2008/0306482 A1* | 12/2008 | Muller | 606/79 |
| 2010/0076442 A1* | 3/2010 | Xie et al. | 606/80 |
| 2011/0144649 A1* | 6/2011 | Victor et al. | 606/80 |

* cited by examiner

*Primary Examiner* — Larry E Waggle, Jr.
(74) *Attorney, Agent, or Firm* — Steven W. Winn

(57) ABSTRACT

An orthopedic bone cutter for cutting bone and tissue is described. The cutting device has a frame on which cutting blades are affixed. The frame is designed with sidewalls that are positioned at an angular relationship with respect to a rotational axis that extends vertically through the cutting device. The cutting blades have a hemispherical side profile with a cutting surface extending from a curved outer distal blade end. The blades are affixed to the frame such that an apex of each of the cutting blades is coincident with the rotational axis at an apex point of the bone cutter.

23 Claims, 11 Drawing Sheets

TILTED BLADE HEMISPHERICAL BONE CUTTER

CROSS-REFERENCE TO RELATED APPLICATION

This application claims priority from U.S. Provisional Patent Application Ser. No. 61/768,159, filed Feb. 22, 2013.

FIELD OF THE INVENTION

The present invention relates to the art of orthopedic cutting devices, more particularly, to an orthopedic cutting device designed to remove bone and tissue from the acetabulum.

PRIOR ART

Reamers are devices intended to remove tissue and bone from the human body. Similarly to that of a traditional reamer device, the orthopedic cutting device of the present invention is designed to remove bone and tissue from the cotyloid cavity of the acetabulum in preparation for the insertion of a hip joint by a prosthetic cup.

In general, traditional prior art acetabular reamers are constructed with a continuous partially hemispherical surface. This partial hemispherical structure is suited to create a cavity in which to fit a prosthetic cup. Prosthetic cups generally have a curved exterior surface that is inserted into the cotyloid cavity.

Prior art reamers are generally constructed such that a series of discrete tissue cutting openings are positioned throughout the outer partially hemispherical surface and extend through the reamer wall thickness. These prior art tissue cutting openings are characteristically designed such that the specific surface that cuts the tissue is provided within the perimeter of the opening.

Many variations of these tissue removing openings have been created, which are generally curved in shape. Other reamers have been designed with "tear drop" or oblong shaped openings. Specific examples of these prior art reamer designs are found in U.S. Pat. Nos. 7,217,272, 6,001,105, and 5,299,893 to Salyer as well as U.S. Pat. No. 6,951,563 to Wolford. In each of these prior art examples, the disclosed reamers embody tissue cutting openings that have a closed perimeter. Furthermore, the tissue cutting surface is enclosed within the perimeter of the opening that lies within the partially hemispherical surface. In other words, the prior art reamers are generally designed with a series of discrete tissue cutting openings. These openings have a continuously closed perimeter with a tissue cutting surface that extends within each opening.

For example, in the '272 patent to Salyer, the disclosed cutting teeth are generally of an oblong shape. The tissue cutting surface is contained within the boundary of the teeth opening. As can be seen in the '272 patent, the tissue cutting surface traverses each opening and is physically bounded by the perimeter of the opening.

In the '105 patent, also to Salyer, the illustrated cutting teeth are generally curved in shape. Similarly to the '272 patent, the tissue cutting surface traverses the width of each opening, and is further contained within the boundary of the tooth opening. The Salyer '893 patent illustrates teeth openings that are generally of a crescent shape. Similarly to the '272 and '105 patents, the tissue cutting surface of the '893 patent is contained within the boundaries of the teeth openings.

The Wolford '563 patent describes a reamer device with cutting teeth openings that are generally of a curved shape. However, unlike the previously described teeth openings attributed to Salyer, the Wolford teeth openings have a raised cutting surface. Although the tissue cutting surface of the '563 patent is not specifically contained within the same surface plane of the opening, the cutting surface is restricted by the dimensions and shape of the discrete opening. The Wolford tissue cutting surface is limited to the relatively small perimeter of the opening. Such a design, as with the previously described Salyer patents, limits tissue contact area. In addition, the relatively small tissue cutting opening of the prior art restricts the flow of debris.

Many problems are associated with these traditional reamer designs. One is that the prior art teeth openings tend to clog with use. As previously mentioned, the prior art reamer tools are generally designed with relatively small openings that restrict the flow of tissue debris. In many cases, a large volume of tissue is excised during a reaming procedure, particularly during an acetabular reaming procedure. The relatively small prior art teeth openings restrict the flow of debris. The teeth openings clog, thus preventing additional tissue removal and reduce the effectiveness of the cutting tool. As a result, the surgical procedure must be halted for the device to be removed, cleaned and reinserted. Removing and reinserting the reamer increases procedure time and further exposes a person to the possibility of infection.

Another problem is that the tissue cutting surface has a relatively small surface area. As previously described, prior art reamers have been designed with tissue cutting surfaces that generally conform to the dimensions of the bounded teeth openings. Such a design limits the surface area of the tissue cutting surface to being contained within the relatively small perimeter of the opening.

Furthermore, the geometry of the cutting edges also affects the efficiency and sharpness of a cutting tool. Preferably, the cutting edges of a surgical tool should be able to cut through a wide variety of tissue and bone. For example, it is desirable for a cutting tool to be able to cut cartilage and bone tissue, ranging from a porous cancellous bone structure to a denser, harder cortical bone structure. Many prior art reamer tools remove tissue by using a scraping action or a tearing action as the reamer cutting teeth pass by. In general, prior art reamers adequately remove tissue from hard bone surfaces but tend to be less effective removing tissue from softer, porous bone surfaces.

Such scraping instruments are described in U.S. Pat. Nos. 3,630,204 and 3,633,583, both to Fishbein. In the '204 patent Fishbein describes a bone cutting blade which is rotatable about an axis where the axis intersects the cutting blade at the cutting edge midpoint. At this intersection, the cutting edge reverses orientation to accommodate approaching bone and tissue that is being cut. The cutting edge is segmented to reduce the amount of contact with the surface being cut and, thus, reduce the cutting force on the blade. In the '583 patent, Fishbein describes a surgical device incorporating cutting blades having a construction to that of the blades described in U.S. Pat. No. 3,630,204. In the '204 patent, Fishbein discloses a device wherein the cutting blades are positioned on the tool such that the cutting edge of the blades lie within a plane that includes the axis of rotation of the device. Thus, the geometry and position of the cutting edge of the blades of the tool that is disclosed, causes tissue and bone to be removed by a scraping action. Such a scraping action is not desired because it could cause bone and tissue to increase in temperature such that damage to the bone and tissue could result. In addition, the scraping action of these tools increases wear rate, causing the cutting surface of these tools to become dull sooner.

Furthermore, these prior art designs limit the ability of a tool design to incorporate additional tissue cutting surface features. These features include the incorporation of different tissue cutting surface textures as well as the ability to create different tissue cutting surface angles. These prior art design limitations impede tissue removal efficiency. Thus, the use of these prior art reamers results in prolonged surgical times, prolonged patient trauma, increased risk of infection and increased medical costs.

The present invention provides a disposable reamer that incorporates design features which address the limitations of the prior art. The features of the reamer of the present invention provide a cost effective disposable cutting device with increased tissue removal efficiency. Therefore, the reamer of the present invention decreases surgical time, minimizes patient trauma, reduces the possibility of infection and reduces overall medical costs.

SUMMARY OF THE INVENTION

The present invention is an orthopedic cutting device designed to cut and remove tissue and bone material. The device is designed to efficiently remove tissue and bone to thereby create a cavity for the insertion of an orthopedic implant. Specifically, the present invention is a bone cutter that is preferably designed to remove tissue and bone from the acetabulum such that an implant cup can be inserted.

The bone cutter of the present invention comprises a frame onto which at least one cutting blade is affixed to an exterior frame surface. The frame is preferably of a wedge shape having a plurality of sidewall surfaces that are angled from a plane that is coincident with a rotational axis of the device. Each of the cutting blades is of a plate like construction having a curved outer profile that extends to a blade apex. A bone cutting surface extends from the convex curvature end of the blade. In addition, the cutting blades may comprise a serrated cutting surface that efficiently cuts through a wide variety of bone and tissue in an efficient manner.

The cutting blades are affixed about the frame such that the bone cutting surface is angled toward the rotational axis of the cutting device. The cutting blades are preferably orientated about the frame such that the apex of each of the respective cutting blades is coincident with the rotational axis of the device. Thus, as the cutting device of the present invention is rotated within the body, a concave cavity of a hemispherical shape is formed. Furthermore, by constructing the cutting device such that the cutting blades are affixed to the exterior of the frame, allows for the unobstructed passage of tissue and contributes to the improved cutting efficiency.

The cutting device of the present invention may also be connected to a shaft driver. The bone cutter of the present invention further comprises a driver interface. The driver interface may comprise a bar and boss configuration or alternatively may be of a cross bar form. The driver interface enables connection of the cutting device to a motor, if desired.

Therefore, the features of the reamer of the present invention provide for increased tissue removal efficiency as compared to prior art reamers. Thus, a reduction in surgical procedure time, patient trauma, infection risk and associated medical costs is achievable.

DETAILED DESCRIPTION OF THE INVENTION

Figure 1:
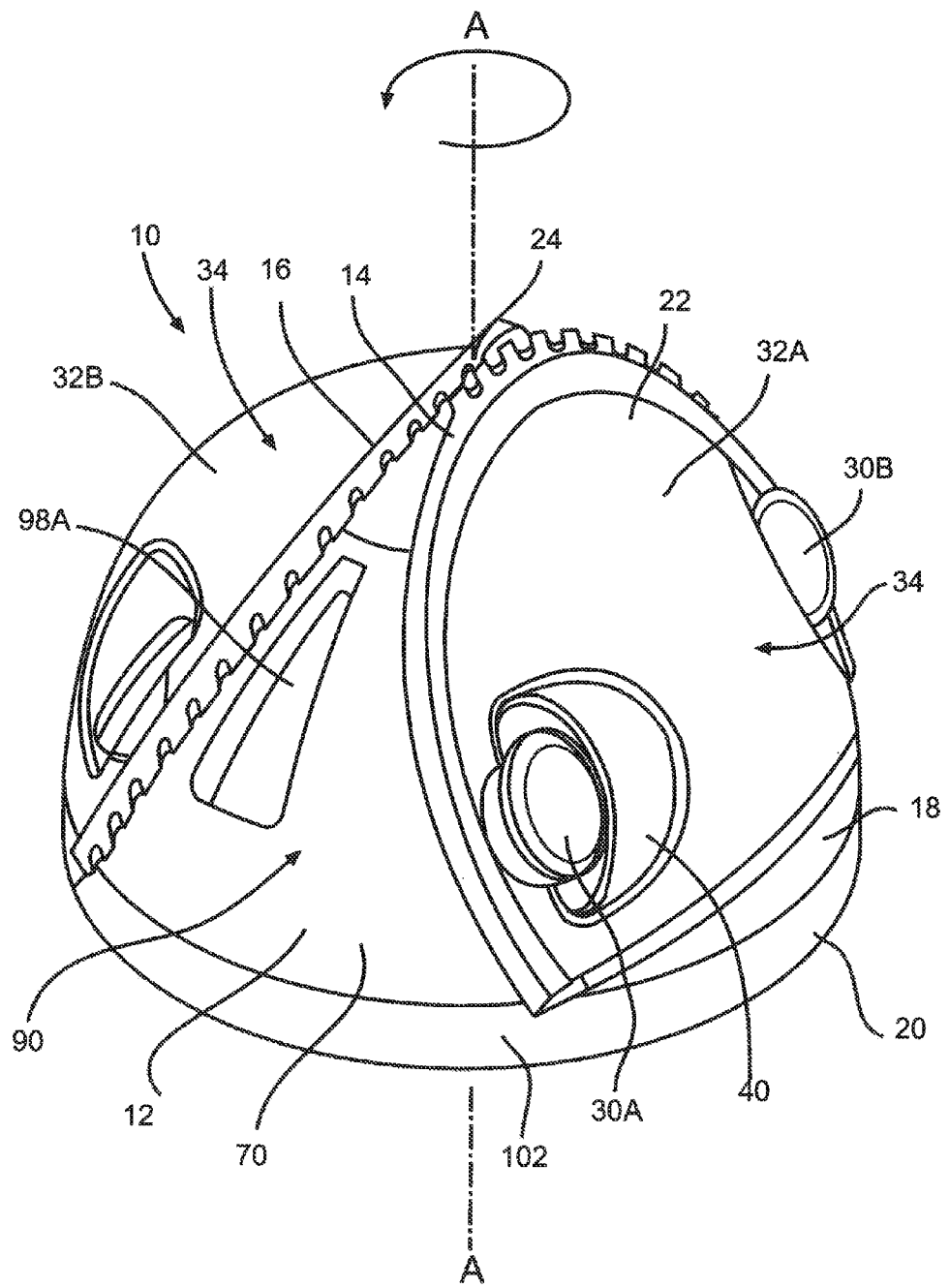
FIG. 1 illustrates a perspective view of an embodiment of the bone cutter of the present invention.

Now turning to the figures, FIGS. 1, 2, 6 and 7 illustrate an embodiment of a bone cutter 10 of the present invention. The bone cutter 10 of the present invention comprises a frame 12 to which is affixed at least a first cutting blade 14. More preferably, as illustrated, the bone cutter 10 of the present invention comprises a first cutting blade 14 and a second cutting blade 16. The frame 12 serves as a structure on which the cutting blades 14, 16 are held. As illustrated in FIG. 1, the bone cutter 10 comprises a base portion 18 having a proximal bone cutter end 20 that extends to a distal bone cutter end 22 having a bone cutter apex point 24. As shown, a rotational axis A-A extends through the apex point 24 adjacent to the distal bone cutter end 22 and is perpendicular to a plane B-B (FIG. 4) at the base portion 44 of the frame 12. The first and second cutting blades 14, 16 are preferably oriented about the frame 12 so that they cut a concave cavity within bone. More preferably, the first and second cutting blades 14, 16 are preferably oriented about the frame 12 such that a concave cavity of a hemispherical form is able to be cut within a bone as the bone cutter 10 rotates about rotational axis A-A. It is noted that the distal end 22 of the bone cutter 10 is preferably contactable to the location of the bone and/or tissue intended to be cut. As previously mentioned, this hemispherical cavity that is formed within the acetabulum is ideally suited to fit a prosthetic cup that is used to receive an implant during a hip replacement surgery. As will be described in more detail, it is the shape of the cutting blades 14, 16 in addition to their preferred angular position with respect to the frame 12 that enables the bone cutter 10 of the present invention to efficiently and accurately form a hemispherical cavity within bone.

Figure 2:
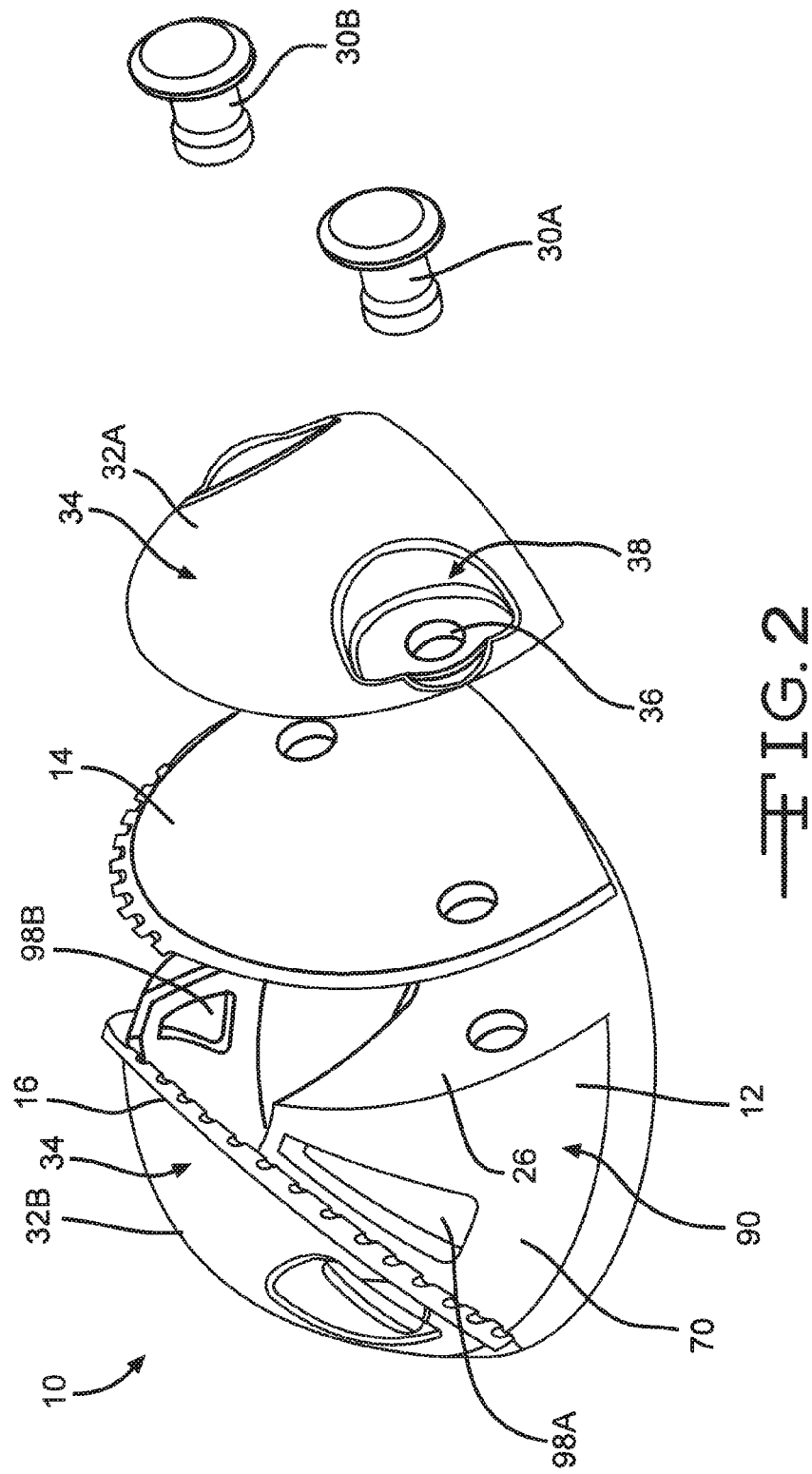
FIG. 2 shows an exploded perspective view of the embodiment of the bone cutter shown in FIG. 1.
Figure 3:
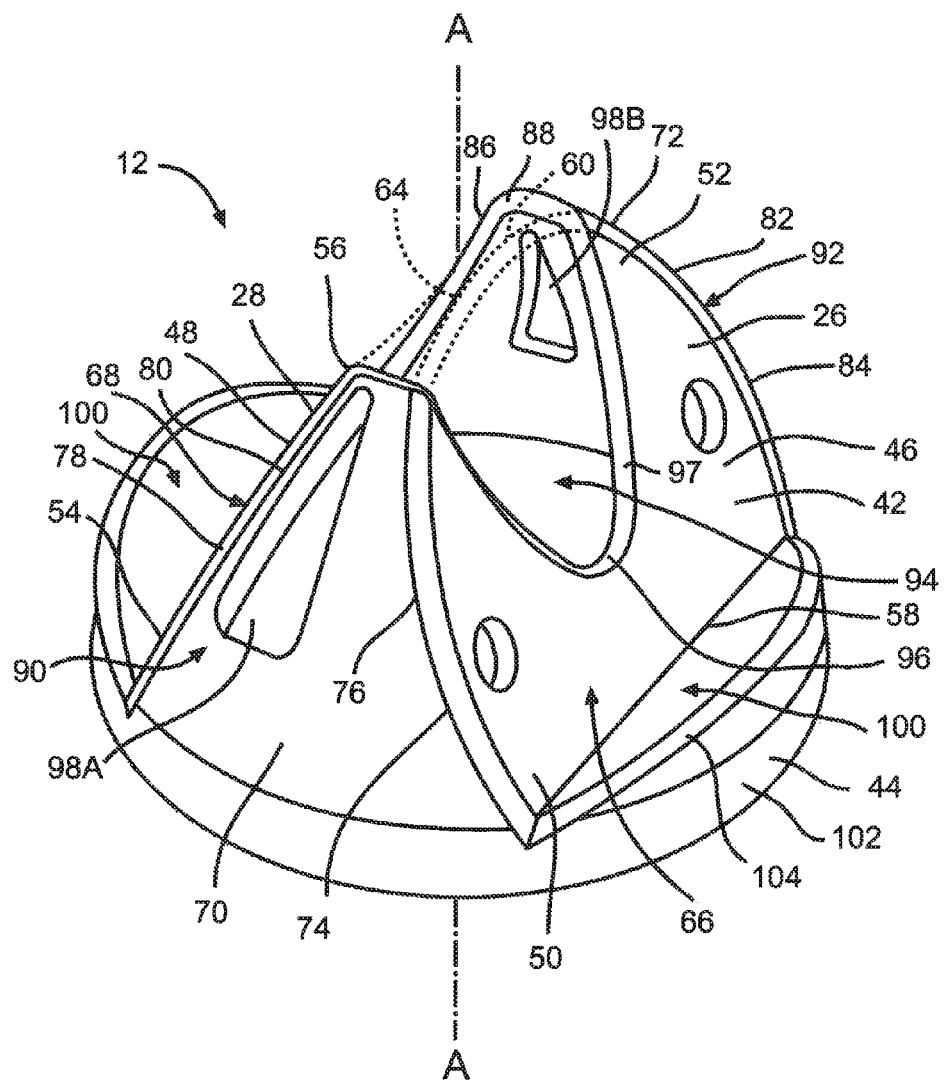
FIG. 3 shows an embodiment of a frame that may be utilized with the bone cutter of the present invention.

FIG. 2 illustrates an exploded view of the embodiment of the bone cutter 10 of the present invention shown in FIG. 1. As shown, the first and second cutting blades 14, 16 are positioned on respective right and left sides 26, 28 of the frame 12 (FIG. 3). As illustrated, rivets 30A, 30B may be used to secure the respective first and second cutting blades 14, 16 to the frame 12. However, other fixation means, such as, but not limited to a screw (not shown), a bolt (not shown), or an adhesive material may be used to affix the cutting blades 14, 16 to the frame 12.

In addition, a blade side cover 32A, 32B may be positioned on the outer side (side facing away from the frame 12) of each of the cutting blades 14, 16. As shown in FIG. 2, a first blade side cover 32A may be positioned in contact with the outer side of the first cutting blade 14. A second blade side cover 32B may be positioned in contact with the outer side of the second cutting blade 16. The blade side covers 32A, 32B, are intended to prevent unintentional contact by cutting blades 14, 16 with adjacent bone and tissue as the cutter 10 is advanced within the body. As illustrated, the blade side covers 32A, 32B have an exterior surface 34 that is curved. This preferably curved exterior surface 34 of the blade side covers 32A, 32B further minimize the potential for unintentional contact by the blades 14, 16 with the surrounding bone and tissue. In addition, the side covers 32A, 32B serve to shield the fixation rivet 30A, 30B or other fixation means from unintentional contact with adjacent bone and tissue as the cutter 10 rotates within the body.

In addition to the curved exterior surface 34, the blade side covers 32A, 32B further comprise throughbores 36 that are preferably recessed within the exterior surface 34 of the blade side covers 32A, 32B. The throughbores 36 receive the shafts of rivets 30A, 30B. As shown in FIG. 2, throughbore 36 resides within recess area 38. In addition, as depicted in FIG. 1, the blade side cover 32A, 32B may comprise a lid portion 40 that is positioned over the rivet 30A, 30B. Similar to the blade side cover 32A, 32B, the lid portion 40 may have a curved exterior surface. The curved exterior surface of the lid portion 40 is also designed to minimize unintentional contact with surrounding tissue.

Figure 4:
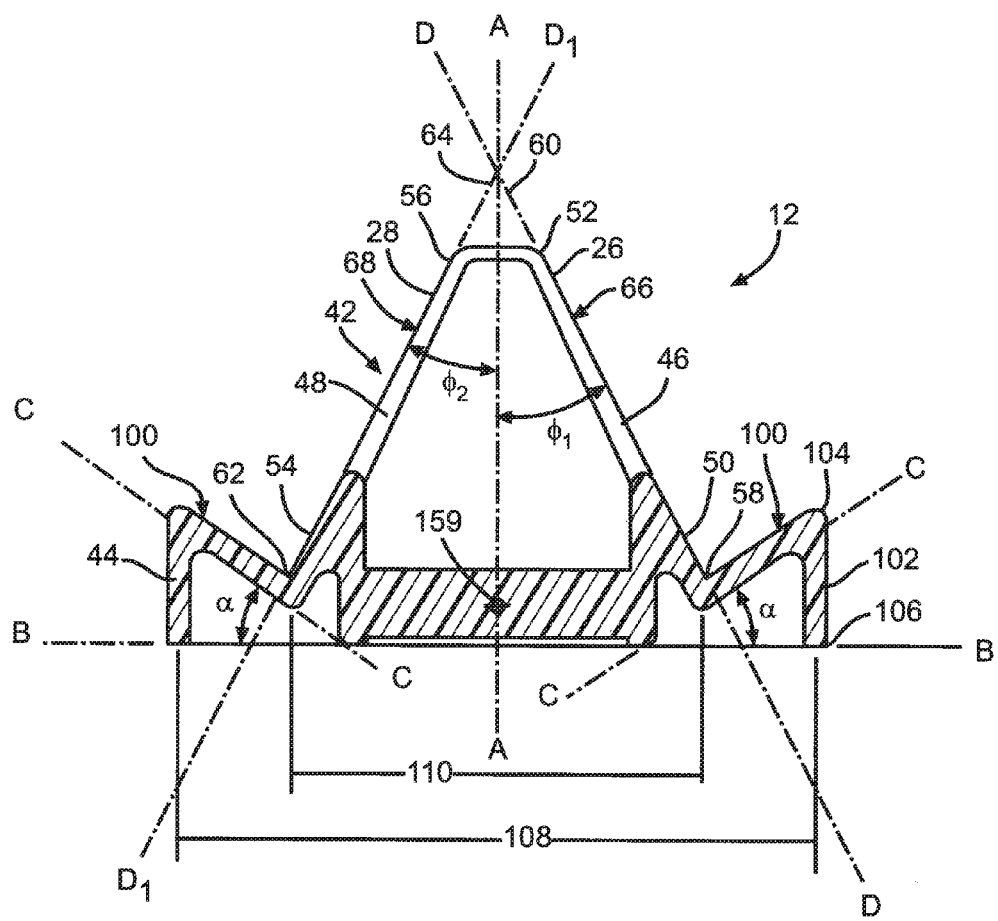
FIG. 4 illustrates a cross-sectional view of the embodiment of the frame shown in FIG. 3.

FIGS. 3 and 4 illustrate an embodiment of the frame 12 of the present invention. Specifically, FIG. 3 illustrates a perspective view of the frame 12 and FIG. 4 illustrates a cross-sectional side view of the frame 12 shown in FIG. 3. As previously mentioned, the frame 12 serves as the structure upon which the cutting blades 14, 16 are affixed. In the embodiment shown, the frame 12 comprises a blade support portion 42 that extends from a frame base portion 44. The blade support portion 42 of the frame 12 preferably comprises a first sidewall 46 and a second sidewall 48 that are positioned at an angular orientation with respect to rotational axis A-A. Each of the first and second sidewalls 46, 48 has a proximal sidewall end that extends to a distal sidewall end. As illustrated in FIGS. 3 and 4, first sidewall 46 extends from proximal sidewall end 50 to distal sidewall end 52. Second sidewall 48 extends from proximal sidewall end 54 to distal sidewall end 56. In a preferred embodiment, the first and second sidewalls 46, 48 are positioned at an angular relationship with respect to rotational axis A-A. Specifically, the distal ends 52, 56 of the respective first and second sidewalls 46, 48 are angled towards rotational axis A-A with the proximal ends 50, 54 of the first and second sidewalls 46, 48 extending from the base portion 44 of the frame 12.

In a preferred embodiment shown in FIG. 3, each of the first and second sidewalls 46, 48 has a side profile that is partially hemispherical in shape. As illustrated, first sidewall 46 comprises a first sidewall base edge 58 that extends to a first imaginary apex 60 (shown in dashed lines). Similarly, second sidewall 48 comprises a second sidewall base edge 62 that extends to a second imaginary apex 64 (shown in dashed lines). The first and second sidewalls 46, 48 are oriented such that the respective sidewall base edges 58, 62 extend upwardly from the base portion 44 of the frame 12 toward the apex 24. Respective imaginary apex points 60, 64 of the first and second sidewalls 46, 48 are angled such that they are preferably coincident with the rotational axis A-A. In addition, first and second sidewalls 46, 48 have external surfaces that are positioned in opposition to each other, both external surfaces facing outwardly from the frame 12. As illustrated, first sidewall 46 comprises external surface 66 and second sidewall 48 comprises external surface 68. In a preferred embodiment both external surfaces 66, 68 may be planar.

Each of the respective first and second cutting blades 14, 16 is positioned in contact with, and affixed to, the respective external sidewall surfaces 66, 68. The preferred planar external surfaces of the first and second sidewalls 46, 48 ensures solid contact of the first and second cutting blades 14, 16 with the respective sidewalls 46, 48 as well as helping to ensure that the cutting blades 14, 16 are oriented at the appropriate angle with respect to rotational axis A-A. In addition, the preferred partial hemispherical shape of these external sidewall surfaces 66, 68 helps facilitate formation of a hemispherical cavity and minimize unintentional tissue contact.

In addition to the first and second sidewalls 46, 48, the frame 12 comprises a third sidewall 70 and a fourth sidewall 72. As illustrated in FIG. 3, the third and fourth sidewalls 70, 72 connect to the first and second sidewalls 46, 48 to thereby form the cutting blade support portion 42 of the frame 12. In a preferred embodiment, the third sidewall 70 is positioned in opposition to fourth sidewall 72. As illustrated, a left edge 74 of the first sidewall 46 meets and joins a right edge 76 of the third sidewall 70. Likewise, a left edge 78 of the third sidewall 70 meets and joins a right edge 80 of the second sidewall 48. A right edge 82 of the first sidewall 46 meets and joins a left edge 84 of the fourth sidewall 72. In addition, a left edge 86 of the second sidewall 48 meets and joins a right edge 88 of the fourth sidewall 72. Thus, the respective first and second sidewalls 46, 48 are joined to the third and fourth sidewalls 70, 72 to thereby form the cutting blade support portion 42 of the frame 12. As illustrated in FIGS. 1-3, the respective right and left edges 76, 88, 78 and 84 of the third and fourth sidewalls 70, 72 are preferably curved such that they seamlessly join respective left and right edges 74, 86, 80, and 82 of the first and second sidewalls 46, 48. In a preferred embodiment, the exterior surfaces of the third and fourth sidewalls 70, 72 are curved. As shown, third sidewall 70 comprises external surface 90 and fourth sidewall 72 comprises external surface 92. As illustrated in FIGS. 1, 2, 3, 6 and 7, exterior surfaces 90, 92 of the third and fourth sidewalls 70, 72 preferably have a partially hemispherical and convex curvature, extending outwardly from the frame 12 with respect to rotational axis A-A. These curved exterior surfaces 90, 92 of the third and forth sidewalls 70, 72 help enable the bone cutter 10 of the present invention to advance toward the intended target of the body to be cut while minimizing the possibility of inadvertently damaging surrounding tissue. As the cutter 10 rotates about rotational axis A-A, the outwardly curved surfaces 90, 92 of sidewalls 70, 72 help to prevent inadvertent cutting and damage to adjacent bone and tissue. Furthermore, the preferred convex exterior surfaces 90, 92 of the respective third and fourth sidewalls 70, 72 help create the preferred concave partially hemispherical cavity within the bone.

Furthermore, it is preferred that the cutting blade support portion 42 has an interior 94 that is hollow. The hollow interior 94 preferably reduces the weight of the frame 12 which enables the bone cutter 10 to rotate at increasing speeds. Thus, by reducing the weight of the frame 12, the bone cutter 10 is able to rotate at increased speeds and cut more efficiently. Moreover, the surgeon performing a surgery is less prone to fatigue from using an overly heavy reamer.

As illustrated in FIG. 3, the frame 12 of the bone cutter 10 may optionally comprise a frame cut out portion 96. As shown, a distal portion of the frame 12 extending from the frame apex 64 toward the base 44 has been removed. As illustrated a "U" shaped portion 97 has been removed from each of the first and second sidewalls 46, 48. It is contemplated that the cut out portion may comprise other geometries such as a rectangle or a circle and is not limited to a "U-shaped" geometry. While not required, this cut out portion 96 improves manufacturability by increasing access to the interior region of the bone cutter 10. In addition, the cutout portion 96 further reduces weight of the device 10, which enables the device to rotate more efficiently at increased speeds and helps prevent fatigue of the surgeon.

In addition, as illustrated in FIGS. 1-3, the frame 12 of the bone cutter 10 of the present invention comprises a first opening 98A that extends through the thickness of the third sidewall 70. In addition, a second opening 98B may extend through the thickness of the fourth sidewall 72. These first and second openings 98A, 98B, which extend through respective third and fourth sidewalls 70, 72, allow for the passage of bone and tissue debris as the bone cutter 10 advances within the body.

As illustrated in FIGS. 3 and 4, the base portion 44 of the frame 12 resides at the proximal end 20 of the cutter 10. In a preferred embodiment, a top surface 100 of the base portion 44 provides a platform surface on which the bottom edges of the respective first and second blades 14, 16 reside. In an embodiment, as shown in FIGS. 3 and 4, a base portion sidewall 102 extends from an outer edge 104 of the top surface 100 of the base portion 44. In a preferred embodiment, the base portion sidewall 102 extends proximally from the top surface 100 of the base portion 44, thereby forming a base portion perimeter 106 with a diameter 108. In a preferred embodiment, the diameter 108 of the base sidewall 102 is greater than a diameter 110 formed at the base of the frame portion 42. This greater diameter 108 of the base portion 44 is preferred to protect the bottom edge of the cutting blades 14, 16 and, thus, reduces the possibility of damage caused to surrounding bone and tissue from inadvertent contact by the bottom edge of the blades 14, 16 as the cutter 10 of the present invention advances within the body. Diameter 110 is measured from where the wall portions providing the top surfaces 100 meet the proximal ends 50, 54 of the respective first and second frame sidewalls 46, 48.

As illustrated, the top surface 100 of the base portion 44 may be angled distally and away from rotational axis A-A. More specifically, as illustrated in FIG. 4, the top surface 100 of the base portion 44 of the housing 12 may be oriented at an angle α formed between imaginary base axis B-B which lies perpendicular to rotational axis A-A and imaginary line C-C which is parallel to the top surface 100 of the base portion 44. In a preferred embodiment angle α may range from about 30° to about 60°. This angular relationship of the top surface 100 of the base portion 44 further protects surrounding tissue and bone from inadvertent damage caused by contact by the bottom edge of the blades 14, 16.

In a preferred embodiment, the frame 12 is composed of a biocompatible material. More specifically, the frame 12 may be composed of a biocompatible polymer, metal or ceramic material. Examples of such polymeric materials include, but are not limited to, acrylonitrile butadiene styrene (ABS), polyarylamides (PARA), polyetherimide (PEI), and polyetheretherketone (PEEK). In addition, examples of metallic materials include, but are not limited to, stainless steel, titanium, MP35N, and a biocompatible metal.

As previously mentioned, it is preferred that the first and second blades 14, 16 are positioned at an angular relationship with respect to each other. Since each of the blades 14, 16 is affixed to the exterior surfaces 66, 68 of the first and second sidewalls 46, 48 of the frame 12, the angular relationship of the blades 14, 16 is primarily determined by the angular position of the respective first and second sidewalls 46, 48. As illustrated in FIG. 4, the exterior surfaces 66, 68 of the first and second sidewalls 46, 48 are oriented at a cutting blade incident angle φ with respect to rotational axis A-A. As shown, the incident angle of the cutting blade is defined by the angle between an imaginary plane that is coincident the respective surface 66, 68 of the first and second sidewalls 46, 48 and the rotational axis A-A. As illustrated in FIG. 4, first cutting blade incident angle $\phi_1$ is defined by the angle between rotational axis A-A and first sidewall imaginary plane D-D. Likewise, second cutting blade incident angle $\phi_2$ is defined by the angle between rotational axis A-A and second sidewall imaginary plane $D_1$-$D_1$. In a preferred embodiment, incident angles $\phi_1$ and $\phi_2$ range from about 5° to about 80°. Both the first and second cutting blade incident angles $\phi_1$, $\phi_2$ may be equal, or different. Preferably, both incident angles $\phi_1$, $\phi_2$ are about 45°. In a preferred embodiment, the first sidewall imaginary plane D-D and the second sidewall imaginary plane $D_1$-$D_1$ intersect the rotational axis A-A adjacent to the apex 24.

Figure 5:
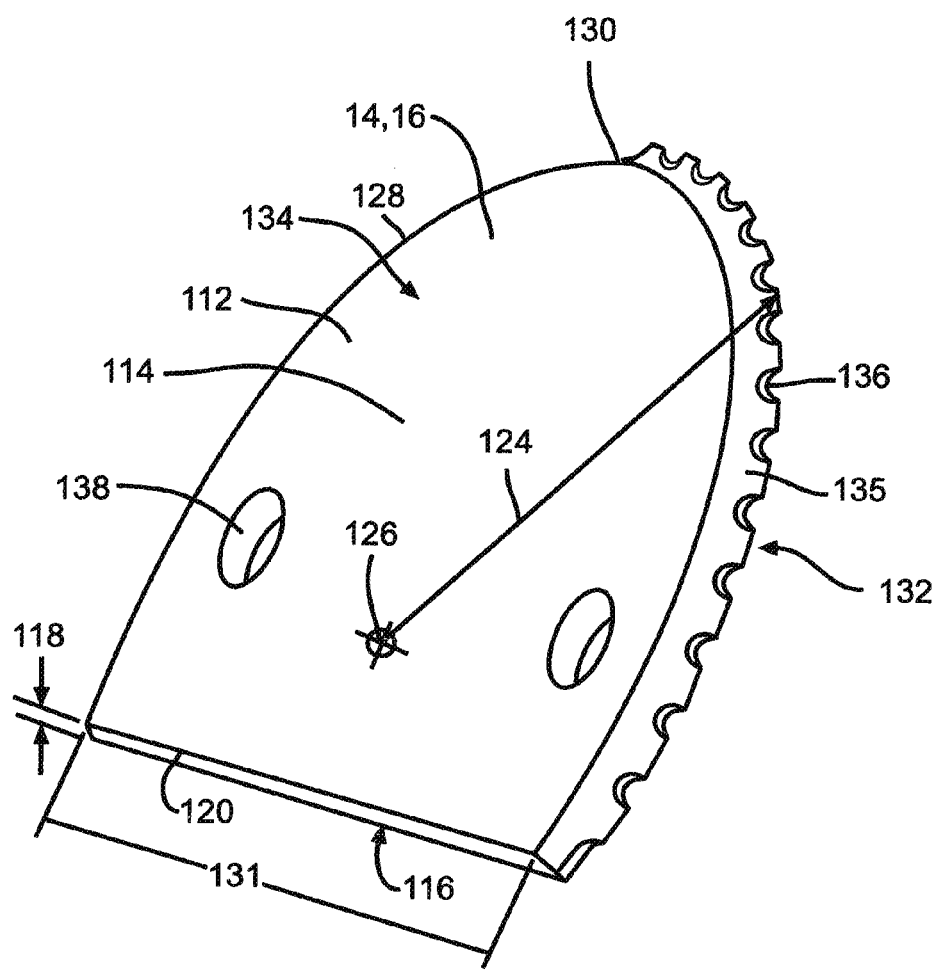
FIG. 5 shows a perspective view of an embodiment of a cutting blade that may be utilized with the bone cutter of the present invention.

FIG. 5 illustrates an enlarged perspective view of a preferred embodiment of the cutting blades 14, 16. It is noted that the cutting blade shown in FIG. 5 is illustrative of both the first and second cutting blades 14, 16. As shown, the cutting blade 14, 16 comprises a blade body portion 112 having a first blade sidewall 114 spaced from a second blade sidewall 116 and a blade thickness 118 therebetween. As illustrated, the blade body 112 extends from a proximal base edge 120, having a base edge length 131, to a curved outer edge 128. In a preferred embodiment, the blade body 112 has a partially hemispherical cross-section. Alternatively, the blade body 112 may have a curved or circular cross-section. As illustrated in FIG. 5, a radial arc 124 extends from a focal point 126 that is positioned at the arc center of the blade body edge 128. The extension of the radial arc 124 sweeps to form the curved outer edge 128 passing through cutting blade apex point 130. Extending from a portion of the outer edge 128 of the blade body portion 112 is a blade cutting surface 132.

In a preferred embodiment, at least one of the first or second blade sidewalls 114, 116 of the first or second cutting blades 14, 16 comprises an exterior surface 134 that is planar. This planar surface 134 is positioned in contact with the exterior surface 66, 68 of the first and second sidewalls 46, 48 of the blade support portion 42 of the frame 12.

As shown in FIG. 5, the cutting surface 132 extends from the outer edge 128 of the blade body 112. In a preferred embodiment, the cutting surface 132 comprises a series of serrated cutting edges having a series of alternating cutting teeth 134 and notches 136. These alternating cutting teeth 134 and notches 136 preferably form the serrated cutting edge, which cuts through bone and tissue. Alternatively, the cutting surface 132 may comprise a blade having a cutting edge that is not serrated, i.e., a razor sharp edge. In a preferred embodiment illustrated in FIG. 5, about half of the outer edge 128 of the cutting blades 14, 16 comprises spaced apart notches 136 forming serrated cutting edges with curved, razor sharp teeth 134 between adjacent notches 136. In addition, the cutting blade 14, 16 may comprise at least one opening 138 that extends through the thickness 118 of the blade body 112. These openings 138 preferably provide a through-bore through which the fixation rivet 32A, 32B may extend.

In a preferred embodiment, each of the first and second cutting blades 14, 16 is positioned on the frame 12 such that the cutting surface 132 extends past the outer edge of the respective first and second frame sidewalls 46, 48. In a preferred embodiment, an inner surface of the blade sidewalls 114 and 116 is positioned in contact with the exterior surface 66, 68 of the first and second sidewalls 46, 48 of the frame 12. In addition, the first and second blades 14, 16 are positioned on the frame 12 such that the respective cutting surfaces 132 are not obstructed by the first and second sidewalls 46, 48 of the frame 12.

In addition, the first and second cutting blades 14, 16 are positioned about the frame 12 such that their cutting surfaces 132 are tilted in the direction of rotation of the cutter 10. In other words, the bone cutter 10 is designed to rotate in the direction of the cutting surface 132. Furthermore, as illustrated in FIG. 1, the cutting blades 14, 16 are preferably positioned about the frame 12 such that their respective cutting surfaces 132 oppose each other. In a preferred embodiment, the cutting surfaces 132 of the first and second cutting blades are angled toward the apex 24 such that a notch 136 of the cutting surface 132 of the first cutting blade 14 is aligned with the razor sharp cutting tooth 135 of the cutting surface 132 of the second cutting blade 16.

In a preferred embodiment, the respective cutting blades 14, 16 are composed of a biocompatible material. More specifically, the cutting blade 14, 16 may be composed of a biocompatible polymer, metal or ceramic material. Examples of preferred metallic materials include, but are not limited to, stainless steel, titanium, MP35N, and a biocompatible metal. Examples of preferred polymeric materials include, but are not limited to, acrylonitrile butadiene styrene (ABS), polyarylamides (PARA), polyetherimide (PEI), and polyetheretherketone (PEEK).

Figure 6:
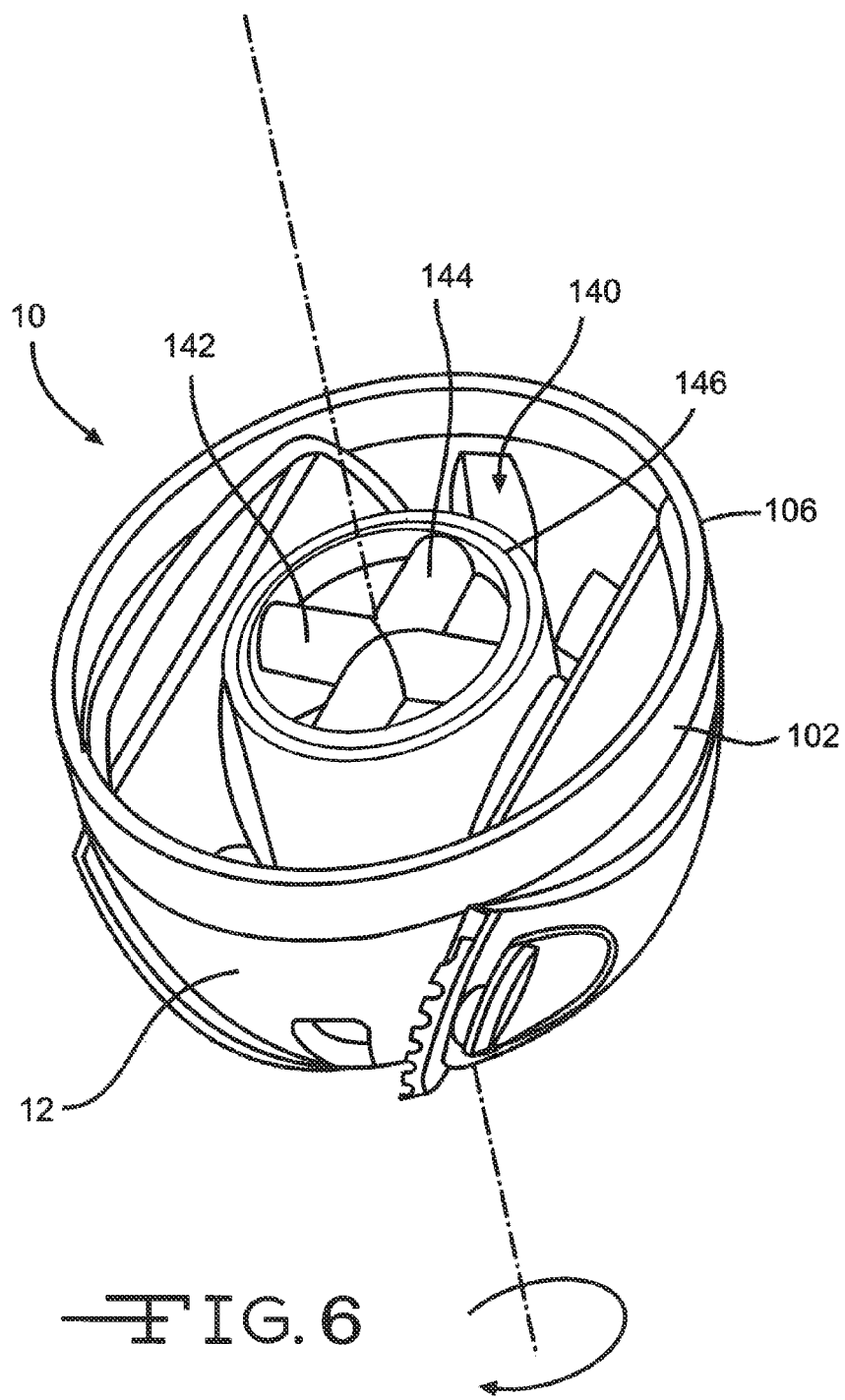
FIG. 6 illustrates an embodiment of a driver shaft interface that may be utilized with the bone cutter of the present invention.
Figure 7:
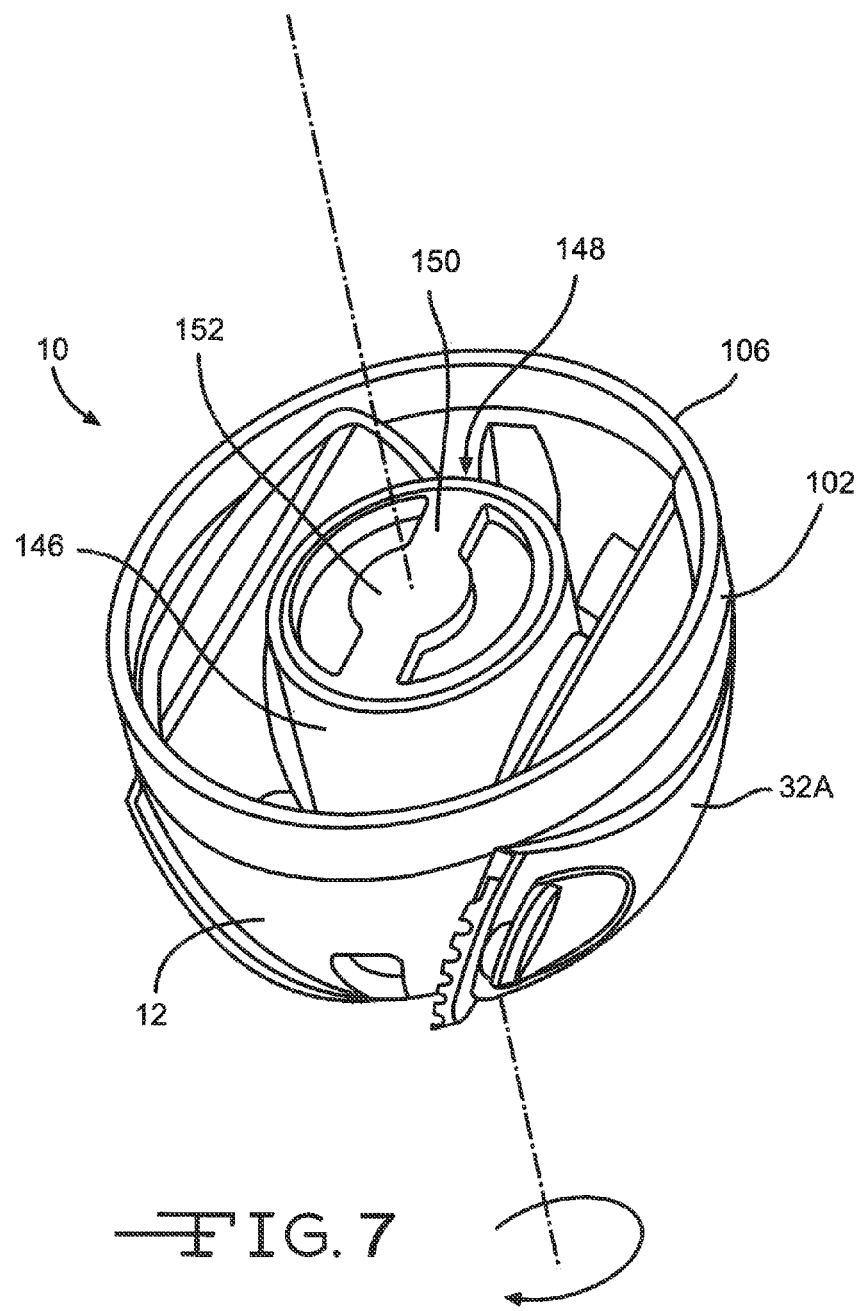
FIG. 7 illustrates an alternative embodiment of a driver shaft interface that may be utilized with the bone cutter of the present invention.

The bone cutter 10 of the present invention is also designed to be connectable to a driver shaft (not shown). FIGS. 6 and 7 illustrate two different embodiments of a driver interface that connects with the driver shaft of a rotary power tool to thereby impart rotational movement to the bone cutter 10 of the present invention. As shown in the embodiment of FIG. 6, the driver interface 140 is of a cross bar design. Specifically, the driver interface 140 comprises a first bar 142 and second bar 144 that are orientated perpendicularly to each other. In the embodiment shown, the bars 142, 144 are of a curved cross-section perpendicular to their length, however, other cross-sectional geometries may be used such as, but not limited to, a rectangular or a triangular cross-section. As illustrated, the bars 142, 144 are positioned within a cylinder 146, which is affixed within the base portion 44 of the frame 12. Alternatively, the bars 142, 144 may span the diameter 108 of the base portion without the need for the cylinder 146.

FIG. 7 illustrates an alternative embodiment of a driver interface 148. As shown, the driver interface 148 comprising a bar and boss interface. This driver interface 148 comprises a bar portion 150 extending to a boss 152. The boss 152 has opposed semi-circular sides meeting the bar portion 150. Similar to the previous crossed bar driver interface 140, the bar and boss interface 148 may also be positioned within a cylinder 146 that resides within the base portion 44 of the frame 12. Alternatively, the bar and boss driver interface 148 may extend across the diameter 110 of the base portion 44 of the frame 12 without the cylinder 146.

Figure 8:
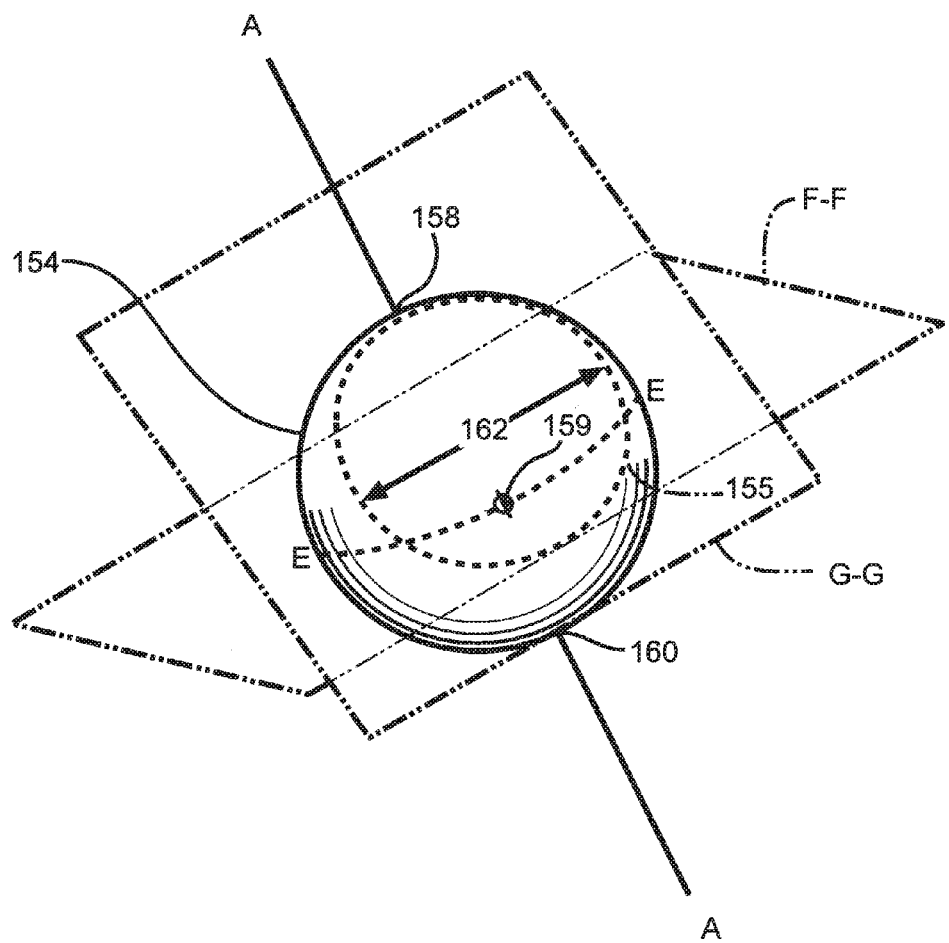
FIGS. 8 and 8A illustrate an example of a preferred orientation of the cutting blade of the present invention with respect to an imaginary sphere having a diameter of a length that is intended to be cut.
Figure 8A:
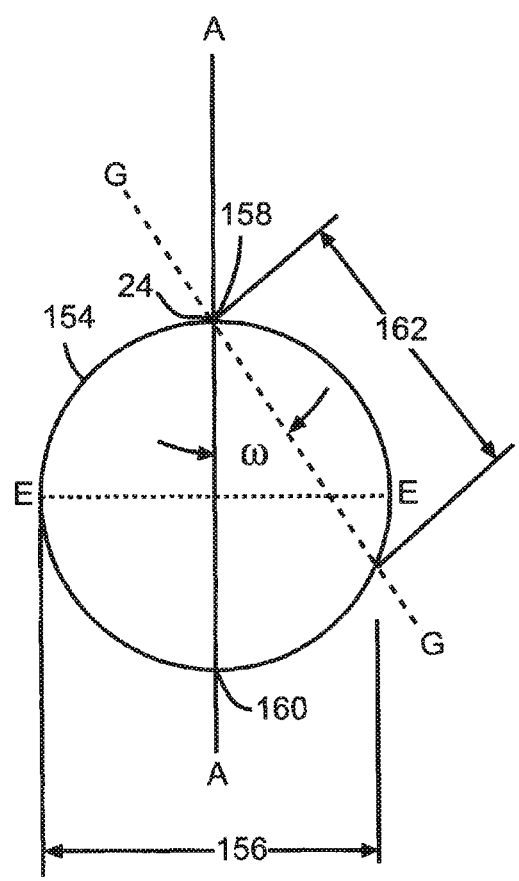

As previously mentioned, the bone cutter 10 of the present invention is intended to cut a cavity of a partially hemispherical concave form within a bone to receive a prosthetic cup therewithin. FIGS. 8 and 8A illustrate the underlying principle of the invention. FIG. 8 illustrates a sphere 154 having an equatorial line E-E that resides within equatorial plane F-F. Rotational axis A-A is shown extending through the sphere 154 from a first pole 158 to a second pole 160. Sphere 154 also comprises an equatorial center point 159 which resides on the equatorial line E-E and between the poles 158 and 160. Referring to FIG. 4, the equatorial center point 159 is the center of the imaginary sphere 154 intended to be cut. FIG. 8A illustrates a side view of the sphere 154 shown in FIG. 8. As shown, sphere 154 has a diameter 156. The equatorial line E-E in this case is not an infinite axis, but is confined to the diameter 156 of the sphere 154. For this example, it is assumed that a concave cavity of diameter 156 (the diameter of the sphere 154) is intended to be cut with the bone cutter 10 of the present invention. As illustrated in FIGS. 8 and 8A, equatorial line E-E is parallel to plane B-B of the base 44 (FIG. 4). As defined herein, the "equatorial line" is a line that is equal to the diameter of a sphere.

As shown, a cutting plane G-G is oriented at a blade incident angle $\omega$ with respect to rotational axis A-A. The intersection of cutting plane G-G with the sphere 154 creates a circle 155 having a cutting diameter 162. It is noted that the cutting edge 132 of cutting blades 14, 16 lies along cutting plane G-G. It is also noted that incident angle $\omega$ is equivalent to the first cutting blade incident angle $\phi_1$ or the second cutting blade incident angle $\phi_2$ as shown in FIG. 4. As the cutting blades 14, 16 rotate about rotational axis A-A, the blades 14, 16 cut a section of the imaginary sphere 154 having a diameter 156. In a preferred embodiment, the length of the cutting diameter 162 is equivalent to two times the length of the arc radius 124 of the cutting blade 14, 16. Thus, as illustrated in FIG. 8A, in order to cut a partially spherical cavity of diameter 156 (the diameter of sphere 154) the imaginary cutting plane G-G must be angled so that it intersects the first pole 158 and the equatorial line E-E. In addition, the cutting diameter 162 of the section of the sphere 154 cut by plane G-G must be wide enough such that the diameter 162 is at least coincident with at least one of the poles 158 or 160 and the equatorial line E-E. The cutting diameter 162 of the section of the sphere 154 cut by plane G-G may be orientated such that it extends beyond the equatorial line E-E. However the cutting diameter 162 and imaginary cutting plane G-G must intersect one of the poles 158, 160 and the equatorial line E-E in order to cut a diameter of the intended partial sphere.

In a preferred embodiment, the diameter 162 of the section of the imaginary sphere 154 that is cut is less than the diameter 156 of the imaginary sphere 154. Because of the preferred angular relationship of the cutting plane G-G with respect to the pole 158, 160 and the equatorial line E-E, the diameter 162 of the section of the imaginary sphere 154 that is cut is less than the diameter 156 of the imaginary sphere 154. As illustrated in FIGS. 8 and 8A, the imaginary cutting plane G-G extends through the first pole 158 and intersects the equatorial line E-E. In addition, cutting diameter 162 is shown intersecting pole 158 and extending past equatorial line E-E. It is noted that the point of intersection of the imaginary cutting plane G-G and rotational axis A-A is the apex point 24 of the cutting device 10 of the present invention. In a preferred embodiment, the cutting diameter 162 intersects with the apex point 24.

However, if the imaginary cutting plane G-G is not oriented at the correct blade incident angle $\omega$ such that it does not intersect one of the poles 158, 160 or intersect the equatorial line E-E of the sphere 154 having a diameter 156 intended to be cut, the resulting cavity will not have a circular cross-section with respect to rotational axis A-A. Likewise, if the cutting diameter 162 is not of the correct dimension to at least be coincident with one of the poles 158, 160 and the equatorial line E-E of the sphere 154, the resulting cavity will not have a circular cross-section with respect to rotational axis A-A. Therefore, it is important that the incident angle $\omega$ between rotational axis A-A and imaginary cutting plane G-G be selected such that the cutting plane G-G is orientated to pass through one of the poles 158, 160 and the equatorial line E-E of a sphere 154 having the desired diameter intended to be cut. In addition, it is also important that the cutting diameter 162 be long enough to at least be coincident with one of the poles 158, 160 and the equatorial line E-E of a sphere 154 having the desired diameter intended to be cut.

Figure 9A:
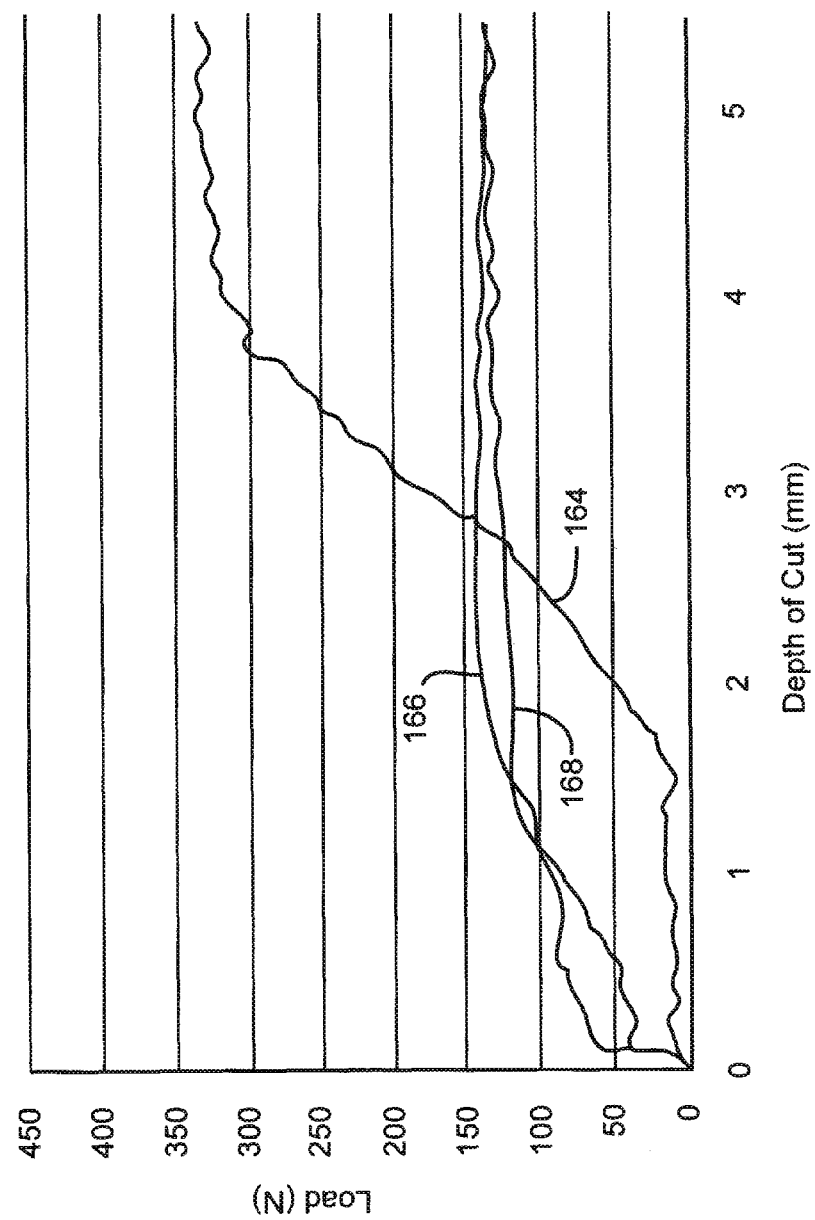
FIGS. 9A and 9B illustrate the results of mechanical testing in which the bone cutter of the present invention was compared against reamers of the prior art.
Figure 9B:
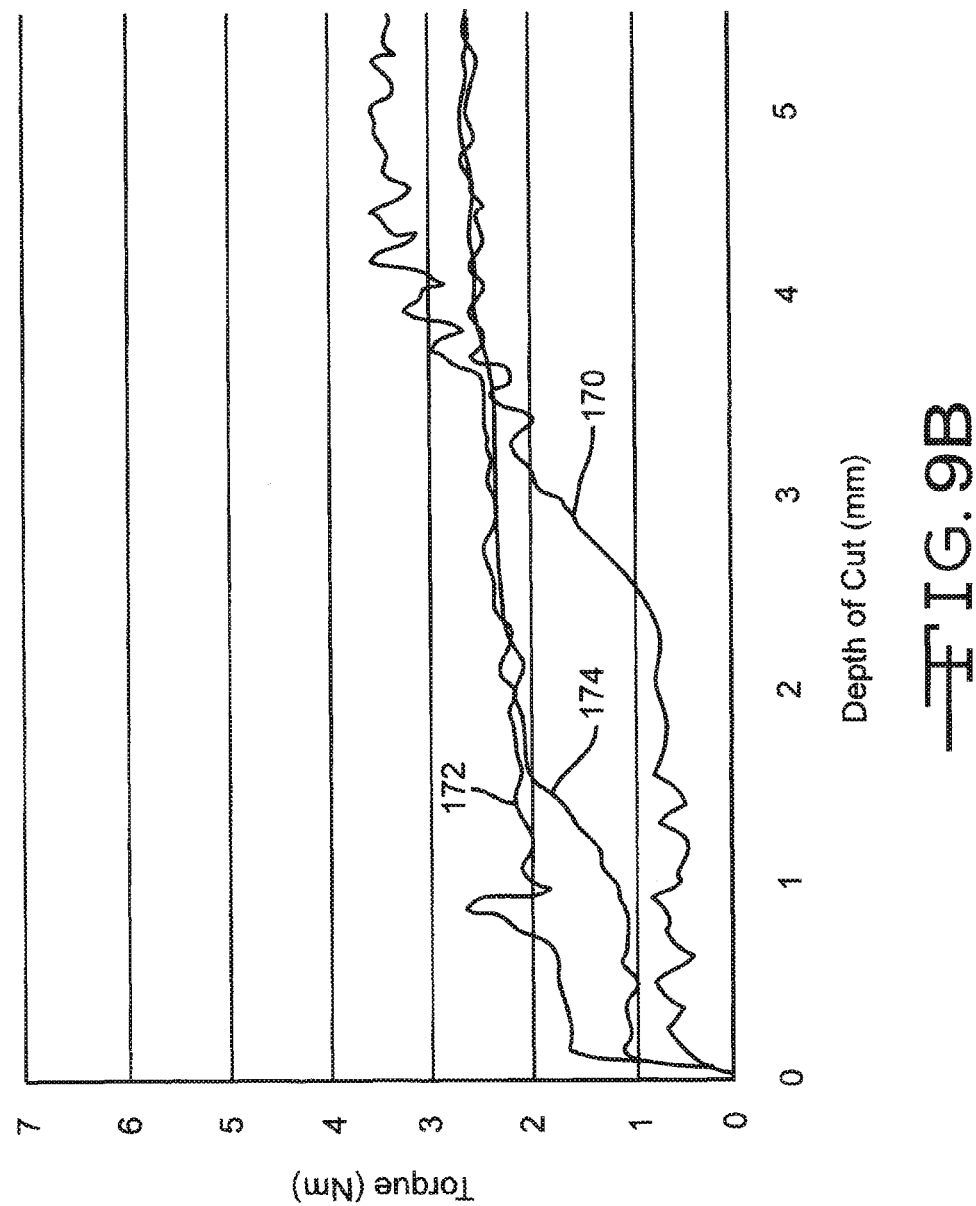

FIGS. 9A and 9B illustrate results of mechanical testing that was performed on the bone cutter 10 of the present invention in comparison to two reamers of the prior art. During the test, both the bone cutter 10 of the present invention and the two prior art reamers were used to cut through a sample of modeling material that is used to simulate bone structure. The modeling material used during the testing is sold under the trade name RenShape® BM5460 and manufactured by Huntsman Advanced Materials of The Woodlands, Tex. As the respective cutting tools advanced through the sample material, axial load (N) and torque (Nm) measurements were taken as a function of cutting depth (mm) into the material.

The prior art reamers were of a traditional orthopedic reamer design having a metal hemispherical shell in which cutting teeth are formed from holes that extend through the thickness of the shell. The first prior art reamer (prior art reamer 1) was constructed according to U.S. Pat. No. 6,001,105 to Salyer. The second prior art reamer (prior art reamer 2) was constructed according to the parameters disclosed in U.S. patent application publication number 2005/0075639 to White et al. Both the bone cutter 10 of the present invention and the two prior art reamers had the same cutting diameter of about 62 mm. During the testing, both the bone cutter 10 of the present invention and the two prior art reamers were rotated at the same rotational speed of 250 RPM and were advanced into the sample material at the same rate of 0.3 mm/sec.

FIG. 9A illustrates the measured axial load (N) being applied by the respective instruments to the sample material as a function of cutting depth (mm). As illustrated in the graph, the measured axial load of the bone cutter 10 of the present invention is represented by line 164 and the measured axial load of the first and second prior art reamers are represent by lines 166 and 168 respectively. Specifically, line 166 of the graph shown in FIG. 9A corresponds to the measured axial load of prior art reamer 1 and line 168 corresponds to the measured axial load of prior art reamer 2. The results of the mechanical testing revealed that a reduced axial load had been applied by the bone cutter 10 of the present invention (line 164) as a function of depth into the modeling material as compared to that applied by prior art reamer 1 (lines 166) and prior art reamer 2 (line 168) up to a depth of about 3 mm. After passing through a depth of about 3 mm, the axial load applied by the bone cutter 10 of the present invention began to increase more than that of the prior art reamers as illustrated from lines 166 and 168. It is noted however, that during a typical hip arthroplasty surgery, a cavity depth greater than about 2 mm is generally not formed within the acetabulum using a reamer of a particular size. To enlarge a reamed cavity, reamers of increasingly greater size are used until the desired reamed profile is obtained. Therefore, the bone cutter 10 of the present invention would most likely apply an axial load of a reduced amount than that of a traditional reamer of the prior art. Such a reduced axial load is generally beneficial because it reduces trauma to the bone.

FIG. 9B illustrates the measured torque being applied by the respective instruments as a function of cutting depth (mm). As illustrated by the graph, the measured torque (Nm) that was applied by the bone cutter 10 of the present invention is represented by line 170. The measured torque (Nm) that was applied by prior art reamer 1 is represented by line 174 and the torque that was applied by prior art reamer 2 is represented by line 172. As shown in the graph, the bone cutter 10 of the present invention applied a reduced amount of torque (Nm) (line 164) as a function of depth into the modeling material than that of the prior art reamers 1 and 2 (lines 174 and 172) to a depth of about 3.5 mm. After passing through a depth of about 3.5 mm, the torque (Nm) being applied to the material by the bone cutter 10 of the present invention increased to an amount that was greater than that being applied by the prior art reamers as illustrated from lines 172 and 174. As previously mentioned, however, a cavity depth greater than about 2 mm, is not typically needed to form a desired reamed profile within the acetabulum during a typical hip arthroplasty surgical procedure. Therefore, the bone cutter 10 of the present invention would most likely apply a reduced amount of torque than that of a traditional reamer of the prior art. Such a reduced amount of torque is beneficial for reducing trauma to the bone.

While the preferred embodiments of the cutting device and methods have been described in reference to the environment in which they were developed, they are merely illustrative of the principles of the inventions. Other embodiments and configurations may be devised without departing from the spirit of the inventions and the scope of the appended claims.

What is claimed is:

1. An orthopedic bone cutter, comprising:
 a) a frame comprising opposed first and second sidewalls extending from a proximal frame end to a distal frame end, a rotational axis extending perpendicularly therethrough, a first imaginary plane co-planar with the first sidewall and a second imaginary plane co-planar with the second sidewall, wherein the first and second sidewalls are positioned at an angular relationship with respect to the rotational axis so that the first and second imaginary planes intersect the rotational axis at a bone cutter apex point positioned at the distal frame end;
 b) a first cutting blade comprising a first blade portion extending from a first proximal base edge to a first distal blade end having a curved perimeter, and a first cutting surface outwardly extending from the curved distal blade end; and
 c) wherein the first blade is affixed to an exterior surface of either the respective first or second frame sidewalls so that the first cutting surface is angled towards the bone cutter apex point.

2. The orthopedic bone cutter of claim 1 wherein a second cutting blade is affixed to the exterior surface of either the respective first or second frame sidewalls, the second cutting blade comprising a second blade portion extending from a second proximal base edge to a second distal blade body end having a curved perimeter, a second cutting surface outwardly extends from the curved distal blade body end.

3. The orthopedic bone cutter of claim 2 wherein the first cutting blade and the second cutting blade are oriented on the frame so that the first cutting surface and the second cutting surface extend in opposing directions.

4. The orthopedic bone cutter of claim 3 wherein a portion of the first and second cutting surfaces are adjacent to each other at the bone cutter apex.

5. The orthopedic bone cutter of claim 1 wherein at least a portion of the first cutting surface comprises a serrated cutting surface having a plurality of alternating cutting teeth and notches.

6. The orthopedic bone cutter of claim 1 wherein at least a portion of the first cutting surface comprises a non-serrated cutting surface.

7. The orthopedic bone cutter of claim 1 wherein the first distal blade end perimeter is defined by a radial arc that extends from a focal point positioned along the first blade base edge.

8. The orthopedic bone cutter of claim 1 wherein the first or the second frame sidewalls comprise an exterior sidewall surface that is planar.

9. The orthopedic bone cutter of claim 1 wherein the frame comprises a third sidewall and a fourth sidewall, wherein the third and fourth sidewalls meet and join the first and second sidewalls so that the first and second sidewalls are positioned adjacent to the third and fourth sidewalls.

10. The orthopedic bone cutter of claim 9 wherein the third and fourth sidewalls have an exterior surface that curves outwardly away from the rotational axis.

11. The orthopedic bone cutter of claim 1 wherein the first cutting blade is positioned on the frame at a first blade incident angle, wherein the first blade incident angle is defined by an angle between the intersection of the first imaginary plane and the rotational axis, the first blade incident angle ranging from about 5° to about 80°.

12. The orthopedic bone cutter of claim 1 wherein a first blade side cover is positioned on a first blade sidewall exterior surface that faces away from the rotational axis.

13. The orthopedic bone cutter of claim 1 wherein the frame is composed of a material selected from the group consisting of acrylonitrile butadiene styrene (ABS), polyarylamides (PARA), polyetherimide (PEI), polyetheretherketone (PEEK), a biocompatible polymeric material, and combinations thereof.

14. The orthopedic bone cutter of claim 1 wherein the first cutting blade is composed of a material selected from the group consisting of stainless steel, titanium, MP35N, a biocompatible metal, and combinations thereof.

15. The orthopedic bone cutter of claim 1 further comprising a shaft driver interface having a bar and boss configuration or a cross bar configuration positioned at the distal frame end.

16. The orthopedic bone cutter of claim 1 wherein the first cutting surface comprises a cutting surface length that is oriented so that it extends past an imaginary equatorial line of a sphere having a diameter length that is intended to be cut.

17. An orthopedic bone cutter, comprising:
a) a frame comprising opposed first and second frame sidewalls extending from a proximal frame end to a distal frame end, a rotational axis extending perpendicularly therethrough, a first imaginary plane co-planar with the first sidewall and a second imaginary plane co-planar with the second sidewall, wherein the opposed first and second sidewalls are positioned at an incident angle with respect to the rotational axis so that the first and second imaginary planes intersect the rotational axis at a bone cutter apex point positioned at the distal frame end;
b) a first and second cutting blade, each cutting blade comprising a blade portion having a first blade sidewall spaced from a second blade body sidewall and a blade thickness extending therebetween, the blade portion extending from a proximal base edge to a distal blade end, wherein a radial arc extending from a focal point positioned along the proximal base edge of the first blade sidewall defines a blade cross-sectional area residing perpendicular to the thickness having a hemispherical shape, and a cutting surface outwardly extending from the distal blade end; and
c) the first and second cutting blades affixed to an exterior surface of the respective first and second frame sidewalls, wherein the first and second cutting surfaces are angled towards the bone cutter apex point.

18. The orthopedic bone cutter of claim 17 wherein at least a portion of the cutting surface comprises a serrated cutting surface having a plurality of alternating cutting teeth and notches.

19. The orthopedic bone cutter of claim 17 wherein the blade incident angle is defined as an angle between the intersection of the rotational axis and the first imaginary plane or the second imaginary plane, the incident angle ranging from about 5° to about 80°.

20. The orthopedic bone cutter of claim 17 wherein the first and second cutting blades are positioned on the frame so that a blade apex point of the respective first and second cutting blades is coincident with the rotational axis at the bone cutter apex point.

21. The orthopedic bone cutter of claim 17 wherein the frame is composed of a material selected from the group consisting of acrylonitrile butadiene styrene (ABS), polyarylamides (PARA), polyetherimide (PEI), polyetheretherketone (PEEK), a biocompatible polymeric material, and combinations thereof.

22. The orthopedic bone cutter of claim 17 wherein the first or second cutting blade is composed of a material selected from the group consisting of stainless steel, titanium, MP35N, a biocompatible metal, and combinations thereof.

23. The orthopedic bone cutter of claim 17 further comprising a shaft driver interface having a bar and boss configuration or a cross bar configuration positioned at the distal frame end.

\* \* \* \* \*